United States Patent [19]

Goldstein et al.

[11] Patent Number: 5,733,505

[45] Date of Patent: Mar. 31, 1998

[54] NON-REGENERATING CARBON MONOXIDE SENSOR

[76] Inventors: Mark K. Goldstein, 2248 Del Mar Heights Rd., Del Mar, Calif. 92014; Vernon T. Taniguchi, 13568 Jadestone Way, San Diego, Calif. 92130; William B. Helfman, 1041 2nd Ave., Chula Vista, Calif. 91911; Michelle S. Oum, 5074 Auburn Dr., San Diego, Calif. 92105

[21] Appl. No.: 579,337

[22] Filed: Dec. 27, 1995

Related U.S. Application Data

[62] Division of Ser. No. 405,262, Mar. 14, 1995.

[51] Int. Cl.$^6$ ................................................. G01N 21/75
[52] U.S. Cl. ........................ 422/83; 422/86; 436/134; 436/166
[58] Field of Search ....................... 422/61, 83, 86; 436/134, 166

[56] References Cited

U.S. PATENT DOCUMENTS

| | | | |
|---|---|---|---|
| 2,153,568 | 5/1939 | Johnson | 177/311 |
| 2,549,974 | 5/1951 | Klug | 23/255 |
| 2,553,179 | 10/1951 | Farr et al. | 23/255 |
| 3,276,004 | 9/1966 | Mayo, Jr. | 340/237 |
| 3,464,799 | 9/1969 | Kimbell | 23/254 |
| 4,023,930 | 5/1977 | Blunck et al. | 23/232 |
| 4,043,934 | 8/1977 | Schuler et al. | 252/186 |
| 4,482,635 | 11/1984 | Herskovitz et al. | 436/134 |
| 4,728,499 | 3/1988 | Fehder | 422/56 |
| 4,879,999 | 11/1989 | Leiman et al. | 128/207.14 |
| 4,994,117 | 2/1991 | Fehder | 436/133 |
| 5,063,164 | 11/1991 | Goldstein | 436/169 |
| 5,293,875 | 3/1994 | Stone | 128/719 |
| 5,302,350 | 4/1994 | Goswami et al. | 422/86 |
| 5,346,671 | 9/1994 | Goswami et al. | 422/86 |
| 5,349,181 | 9/1994 | Saini et al. | 250/227.14 |
| 5,357,971 | 10/1994 | Sheehan et al. | 128/719 |
| 5,383,469 | 1/1995 | Vreman et al. | 128/719 |
| 5,404,885 | 4/1995 | Sheehan et al. | 128/716 |
| 5,405,583 | 4/1995 | Goswami et al. | 422/86 |

OTHER PUBLICATIONS

Shepard M., "Rapid Determination of Small Amounts of Carbon Monoxide", *Analytical Chemistry*, Feb., 1947, vol. 19, pp. 77–81.

*Primary Examiner*—Lyle A. Alexander
*Attorney, Agent, or Firm*—Christie, Parker & Hale, LLP

[57] ABSTRACT

A carbon monoxide (CO) detection system is connected into an anesthesia gas delivery system. The system comprises, among other things, a CO sensor unit containing an inexpensive, replaceable sensor that detects the presence of CO in anesthesia, an in-line adapter that exposes the detection unit to the main stream of the gas and can be placed in a variety of different locations along the gas stream and a side-stream adapter for the removal and analysis of gas stream samples using a CO sensor unit outside of the main gas stream. There is also apparatus capable of measuring the response of the sensors to CO exposure, and data acquisition and a data processing unit for storing, processing and displaying the CO sensor response data. In a preferred embodiment there is a carbon monoxide detection system comprising a detection unit including a sensor unit and a measurement unit. The sensor unit detects carbon monoxide based on the change or rate of change of the optical characteristics of the sensor unit. In a specific embodiment a non-regenerative carbon monoxide sensor comprises a mixture of palladium chloride, silicomolybdic acid, and sulfurous acid. The non-regenerating sensor comprises an antioxidant, preferably sulfite ion.

10 Claims, 8 Drawing Sheets

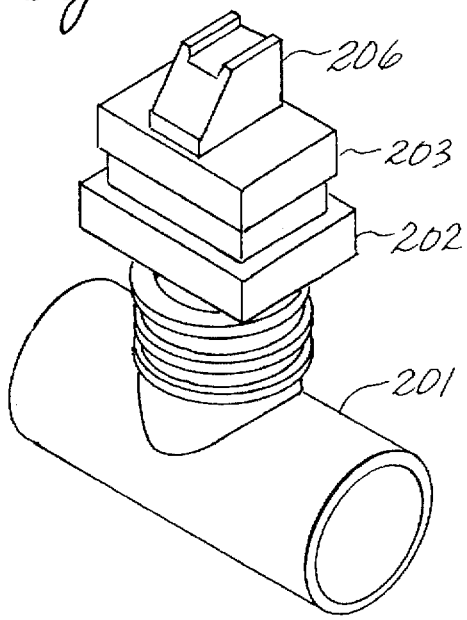
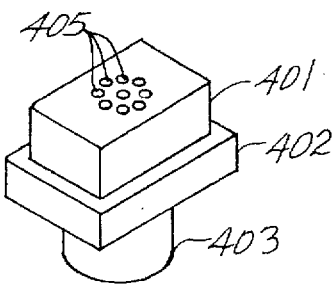
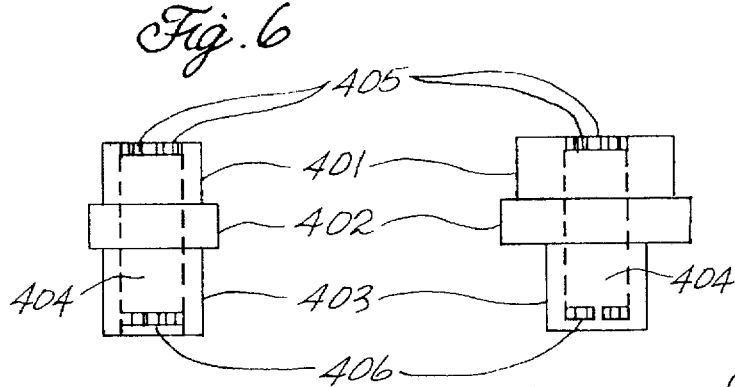
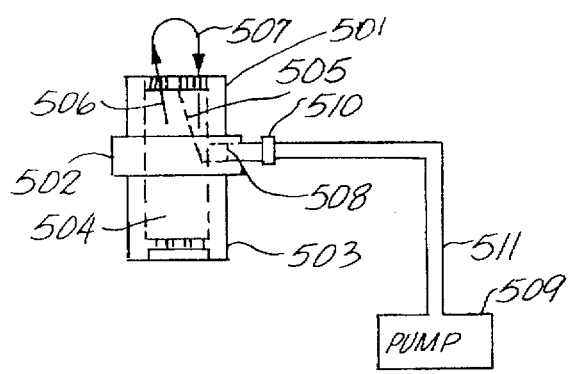

ZERO AIR
NON-REGENERATING SENSOR

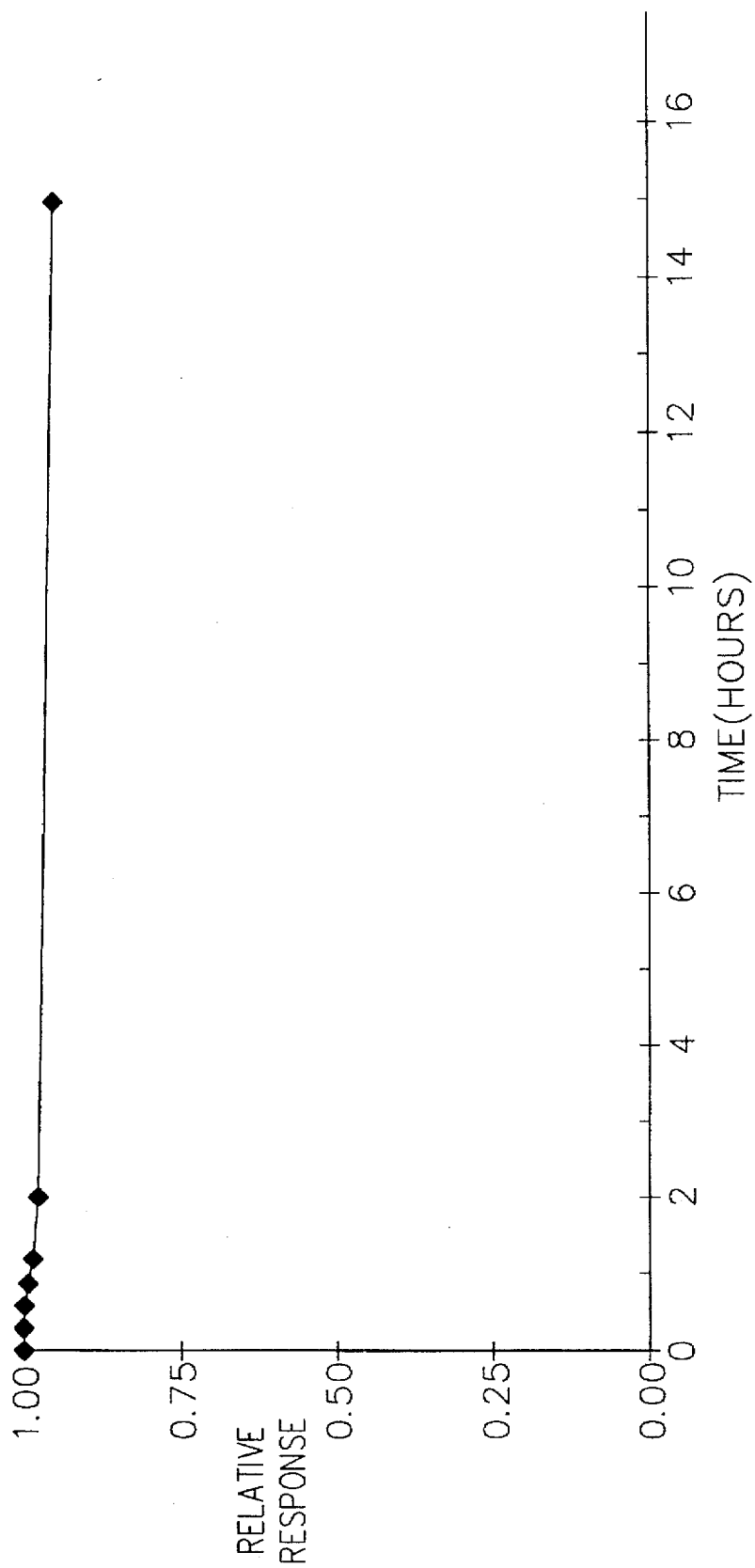

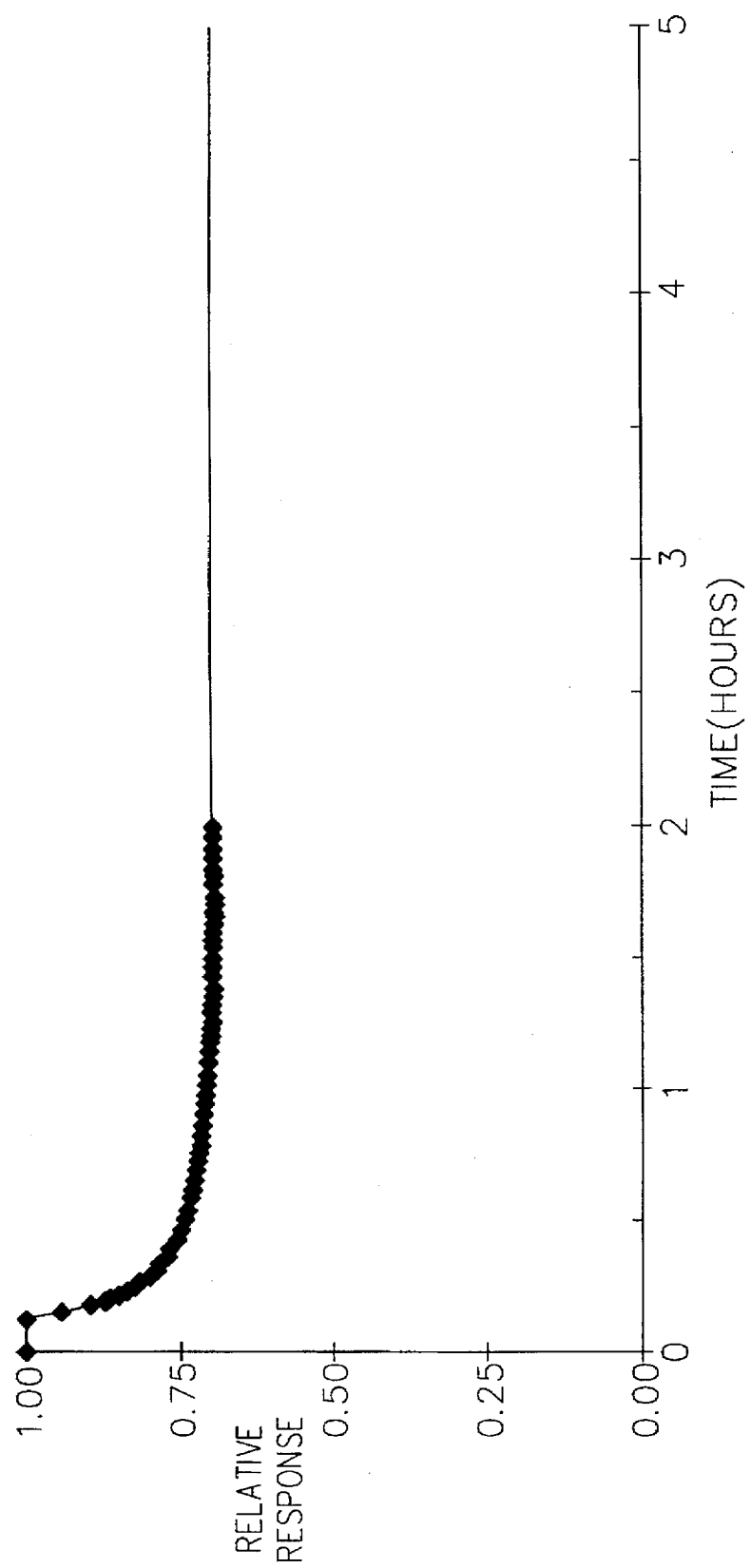

NON-REGENERATING CARBON MONOXIDE SENSOR

This application is a division of U.S. patent application Ser. No. 08/405,262 filed Mar. 14, 1995.

FIELD OF THE INVENTION

The present invention relates to the detection of carbon monoxide in gas delivery systems, and more particularly, to novel sensor for continuous monitoring of the concentration of carbon monoxide in gases in closed, semi-closed or open gas systems by measuring the change and/or the rate of change of the optical characteristics of a sensor exposed to the gases.

BACKGROUND OF THE INVENTION

The effects and response of patients to general inhalational anesthesia is controlled by the anesthesiologist by varying the amounts of modern volatile anesthetic gases, such as desflurane, enflurane, isoflurane and other halogenated gases, combined in a carrier gas mixture of oxygen ($O_2$), air and/or nitrous oxide ($N_2O$). Despite the fact that these newer halogenated volatile anesthetic gases have only been introduced over the last several years, their use is prevalent and widespread. Approximately 23 million surgical procedures are performed each year requiring anesthesia and many more medical procedures are performed each year requiring other medically important gases such as air or oxygen, in the United States alone.

Carbon monoxide (CO) is a deadly gas that is odorless, colorless and tasteless. Its toxic properties and ill effects on humans are well documented and the mechanisms of CO poisoning are well understood. Hemoglobin, the oxygen carrying component in red blood cells, has an affinity for CO that is some 200 times greater than that for oxygen. Carbon monoxide in inspired gases readily competes with $O_2$ to form carboxyhemoglobin (COHb) thus limiting the transport of oxygen throughout the body. Symptoms of CO poisoning include; headaches, dizziness, drowsiness, fatigue, nausea, vomiting, loss of higher cognitive abilities and if exposure levels are high enough, unconsciousness and death. Recovery from CO poisoning is slow and in severe cases, hyperbaric oxygen treatment is required to prevent death.

Despite the high purity standards established for anesthetic gases, CO poisoning of patients has occurred when modern halogenated volatile anesthetic and other gases have been administered. In one specific case reported in the literature, the arterial blood gas report (i.e., CO-Oximeter measurements) for a patient under anesthesia showed a COHb level of 31.5%. (Lentz, Robert E., "CO Poisoning During Anesthesia Poses Puzzles" *Anesthesia Patient Safety Foundation Newsletter* 1994; 9: 13–14). Recent evidence indicates that a source of CO contamination is the reaction of halogenated volatile anesthetic gases with dry carbon dioxide ($CO_2$) adsorbents in anesthetic gas circuits. (Fang, Z. X., Eger, E. I., II, "Source of Toxic CO Explained: —$CHF_2$ Anesthetic+Dry Absorbent", *Anesthesia Patient Safety Foundation Newsletter* 1994; 9: 25–30).

Exposure of the halogenated volatile anesthetics desflurane, enflurane, or isoflurane to dry Baralyme® (Ba(OH)$_2$ mixed with NaOH and/or KOH) or dry Sodasorb® (Ca(OH)$_2$ mixed with NaOH and/or KOH) has been shown to cause the decomposition of the halogenated anesthetic gases resulting in the formation of CO. For example, peak concentrations of 19,700 parts per million (ppm) CO were found in an anesthetic gas containing 4% desflurane from the reaction of the gas with dry Baralyme®. (Fang, Z. X., Eger, E. I., II, "Source of Toxic CO Explained: —$CHF_2$ Anesthetic+Dry Absorbent", *Anesthesia Patient Safety Foundation Newsletter* 1994; 9: 25–30). Even after four hours of constant gas flow, the anesthetic gas containing 4% desflurane continued to react with the dry Baralyme®, generating a CO concentration of 2,070 ppm. The average value of the CO concentration for a four hour period of delivery of an anesthetic gas containing 4% desflurane was reported to be 4,700 ppm.

To someone knowledgeable in the art, these high levels of CO exposure are of great concern. The U.S. Environmental Protection Agency has set standards for outdoor exposure to CO at 9 ppm over 8 hours or 35 ppm over 1 hour, neither of which should be exceeded more than once a year. (United States Environmental Protection Agency, "Revised Evaluation of Health Effects Associated with Carbon Monoxide Exposure: An Addendum to the 1979 EPA Air Quality Criteria Document for Carbon Monoxide." 1984, EPA-600/8-83-033F. Environmental Criteria and Assessment Office. U.S. Environmental Protection Agency, Research Triangle Park, N.C.)

Other studies have identified certain sensitive groups of people that are especially susceptible to CO poisoning, including pregnant women, fetuses, infants, the elderly, people at high altitude, people suffering from anemia, people with obstructive pulmonary disease, and people with coronary artery disease. (Traynor, G. W., Apte, M. G., Diamond, R. C., Woods, A. L., "A Carbon Monoxide Passive Sampler: Research and Development Needs" 1991, LBL-26880. Lawrence Berkeley Laboratory, Berkeley, Calif. and references therein).

Presently, CO in anesthesia gas machines and other rebreather machines is removed by flushing the entire gas system with 100% $O_2$ and/or changing the existing "old" Baralyme® or Sodasorb® for new, hydrated material prior to use. These procedures are expensive, time consuming and do not assure that all the CO has been removed or that CO may not later form and go undetected while the gas system is in use.

Gas analyzing equipment is not commercially available that can accurately and economically detect and measure CO concentrations in anesthetic gas streams being administered to patients. Commercial infrared (IR) and electrochemical cell (EC) based gas analyzers are not suitable for in-line and/or side-stream detection and quantitative measurement of CO in gas streams. Interference from carbon dioxide gas, moisture, nitrous oxide and/or other gases limits the usefulness of IR gas sensor instruments for the detection of CO.

In EC based gas analyzers employing platinum electrodes, halogenated volatile organics and other gases are known to interfere with CO detection. As a result, EC based detectors are found to be unreliable and inaccurate in their response and ability to measure CO.

The current costs for commercial IR gas analysis instruments and EC gas analysis instruments are in the range of $6000 to $10,000 per unit and $1000 to $3000 per unit, respectively. Therefore, detection and monitoring of CO in anesthesia gas machines with either of these two commercial gas analysis technologies is expensive and unreliable.

It is, therefore, desirable that a carbon monoxide detection system be devised that can detect and monitor the level of CO in anesthetic gases and other medically administered gases. The ideal characteristics of such a system are: (1) that combinations of the anesthetic gases and/or other inhaled gases do not interfere with the CO sensor response; (2) that the system accurately detect and monitor the levels of any CO present; (3) that the system inform the attending anesthesiologist of the cumulative CO exposure to the patient over the entire course of the operation; (4) that the system inform the attending anesthesiologist of the "real time" level of CO in the gas streams; (5) that the system be easy to use by the anesthesiologist; (6) that the system be easily adapted to current medical gas systems and equipment and; (7) that the system be economical to purchase and operate.

In the U.S. Pat No. 5,063,164: BIOMIMETIC SENSOR THAT SIMULATES HUMAN RESPONSE TO AIR-BORNE TOXINS, (the contents of which are hereby incorporated by reference) and the related pending U.S. patent application Ser. No. 08/297,141: PHOTON ABSORBING BIODERIVED ORGANOMETALLIC CARBON MONOXIDE SENSORS, (the contents of which are hereby incorporated by reference) Mark K. Goldstein and others describe an economical CO gas sensor, which is self-regenerating at about the same rate as a human recovering from CO poisoning. The sensor consists of a transparent or semi-transparent porous solid substrate impregnated with a self-regenerating chemical reagent that mimics human hemoglobin. The presence of carbon monoxide is detected by measuring the darkening of the sensor upon exposure to CO. The sensor is able to self-regenerate and return to its original transparency when CO is no longer present. This CO gas sensor technology has reached commercialization in the form of cost-effective residential, recreational vehicle and commercial CO gas alarms.

A means of measuring the rate of change of the sensor's response to CO and subsequent regeneration over time is described in the U.S. patent application Ser. No. 08/303,357: APPARATUS AND METHOD FOR ENHANCING THE RESPONSE OF A BIOMIMETIC SENSOR, the contents of which are hereby incorporated by reference.

SUMMARY OF THE INVENTION

The present invention comprises a means and method for detecting carbon monoxide (CO) in the flow of closed, semi-closed and open gas delivery systems, and most particularly a non-regenerating carbon monoxide sensor. In a preferred embodiment there is a carbon monoxide detection sensor unit comprising means for detecting carbon monoxide based on the change of rate of change of the optical characteristics of the sensor unit. In a specific embodiment a non-regenerative carbon monoxide sensor comprises palladium chloride, silicomolybdic acid, and sulfurous acid. The non-regenerating sensor comprises an antioxidant, preferably sulfite ion.

BRIEF DESCRIPTION OF THE DRAWINGS

These and other features and advantages of the present invention will become appreciated as the same becomes better understood with reference to the specification, claims and drawings wherein:

FIG. 2 is an isometric view of the assembly of a sensor unit, adapter unit and a commercially available T-piece;

FIG. 5 is an isometric view of an adapter unit for the in-line detection of CO;

FIG. 6 is a side view of the adapter unit of FIG. 5;

FIG. 7 is a partially schematic side view of an adapter unit for side-stream detection of CO constructed according to principles of this invention;

FIG. 10 is a chart illustrating in graphical form the response of the non-regenerating sensor unit prepared according to principles of this invention subjected to a representative anesthetic mixture of 6% Ethrane in a mixture of 50% nitrous oxide: 50% oxygen as set forth in Table 4; and FIG. 11 is a chart illustrating in graphical form the response of the non-regenerating sensor unit prepared according to principles of this invention subjected to a mixture of 100 parts per million carbon monoxide in zero air as set forth in Table 8.

DETAILED DESCRIPTION OF THE INVENTION

Figure 1:
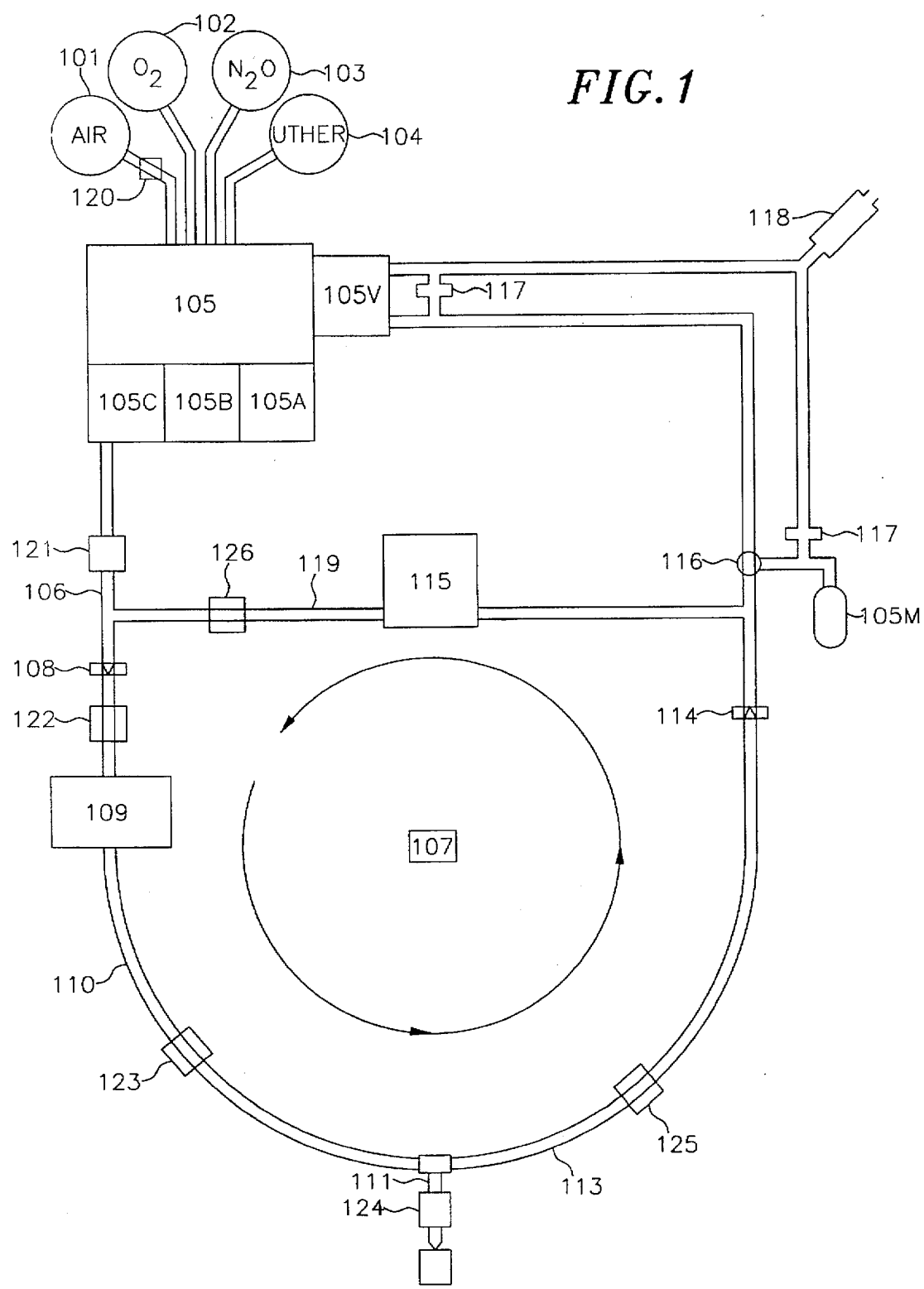
FIG. 1 is a schematic view of an anesthetic gas machine incorporating the carbon monoxide detection systems according to principles of this invention.

The present invention comprises of a means and method of detecting carbon monoxide (CO) in the flow of closed, semi-closed or open gas delivery systems, devices for incorporating CO detectors into gas delivery systems and a non-regenerating toxic gas sensor. FIG. 1 is a schematic view of an anesthetic gas machine illustrating the incorporation of the carbon monoxide detection systems constructed according to principles of the present invention. Sources of gaseous air 101, $O_2$ 102, $N_2O$ 103, and other gases 104, flow through gas lines into a conventional gas mixing and ventilating unit 105 containing vaporizers 105a and 105b, a mechanical ventilating system 105v and a volatile anesthesia administration system 105c.

The gas mixture leaves the gas mixing and ventilating unit 105 and enters the gas recirculating system through a fresh gas inlet 106. The direction of the gas flow in the gas recirculating system is indicated by an arrow 107. A mixture of fresh gas and recirculated gas passes through an inhalation check valve 108 and then enters a humidifying unit 109. From the humidifying unit 109, the gas flows through the inspiratory limb 110 to a Y-piece 111 and then into the patient 112.

When the patient exhales the exhaled gas enters the expiratory limb 113 and goes through an expiratory check valve 114. The exhaled gas either enters a $CO_2$ absorption unit 115 or is directed by a ventilator mode valve 116 to the mechanical ventilating system 105v or the manual ventilating system 105m. Gas can exit the system through either of two anesthesia purge valves 117 thus entering a room gas scavenging system 118. The gas exiting the $CO_2$ absorption unit 115 is recirculated into the gas recirculating system by a recirculated gas line 119. Commercially available T-pieces (not shown) can be placed in a variety of different places as indicated by the boxes 120, 121, 122, 123, 124, 125 and 126 allowing for the detection of CO in any of a variety of places in the gas stream according to principles of this invention.

Figure 3:
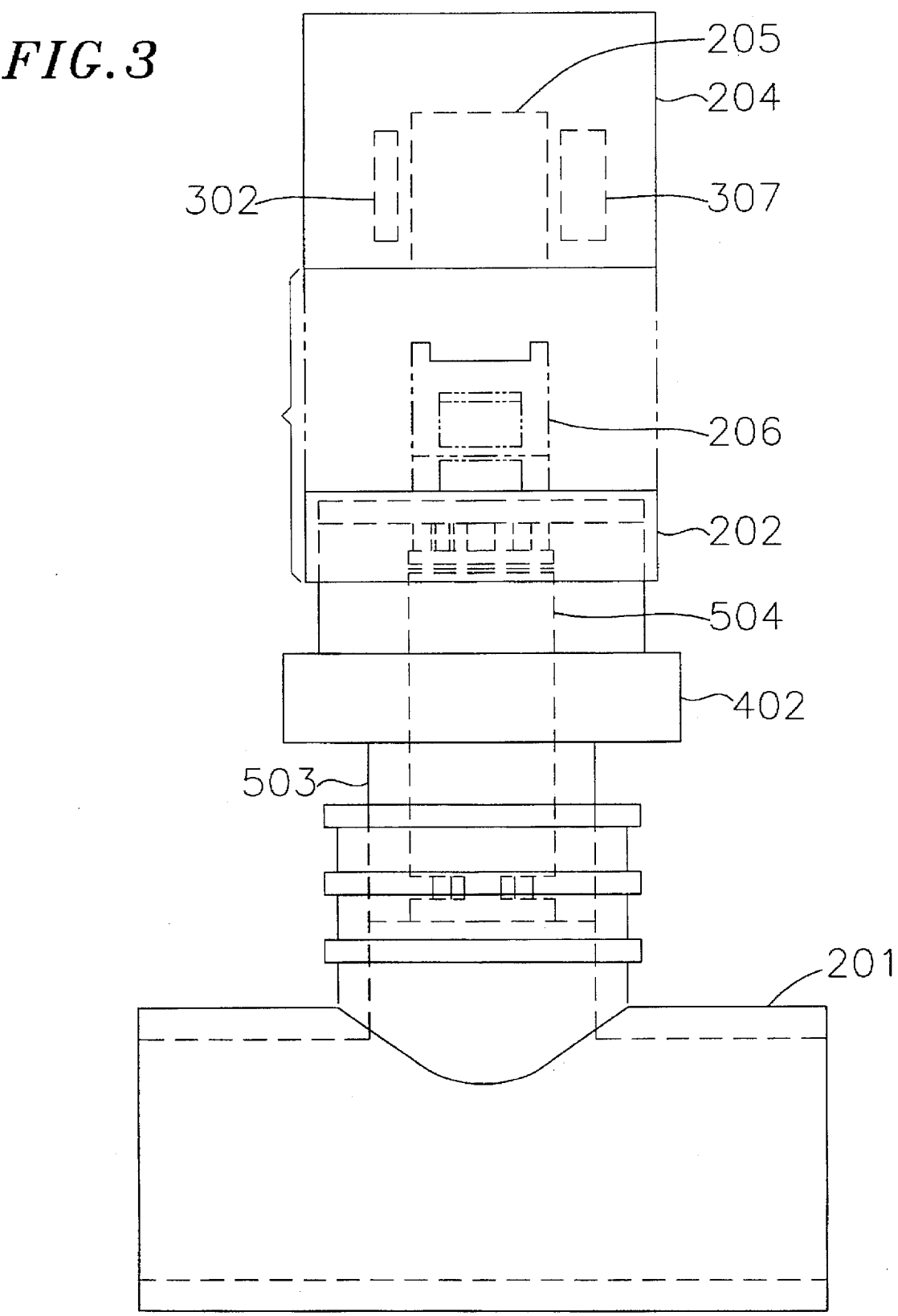
FIG. 3 is a side view of the assemble of FIG. 2.

This aspect of the invention is illustrated in greater detail in FIGS. 2 and 3 which show the assembly of a commercially available T-piece 201, an adapter unit 202, a sensor unit 203, and a measurement unit 204 illustrated exploded from the sensor unit. The measurement unit has a cavity 205 which fits closely around a sensor housing 206 atop the sensor unit.

Figure 4:
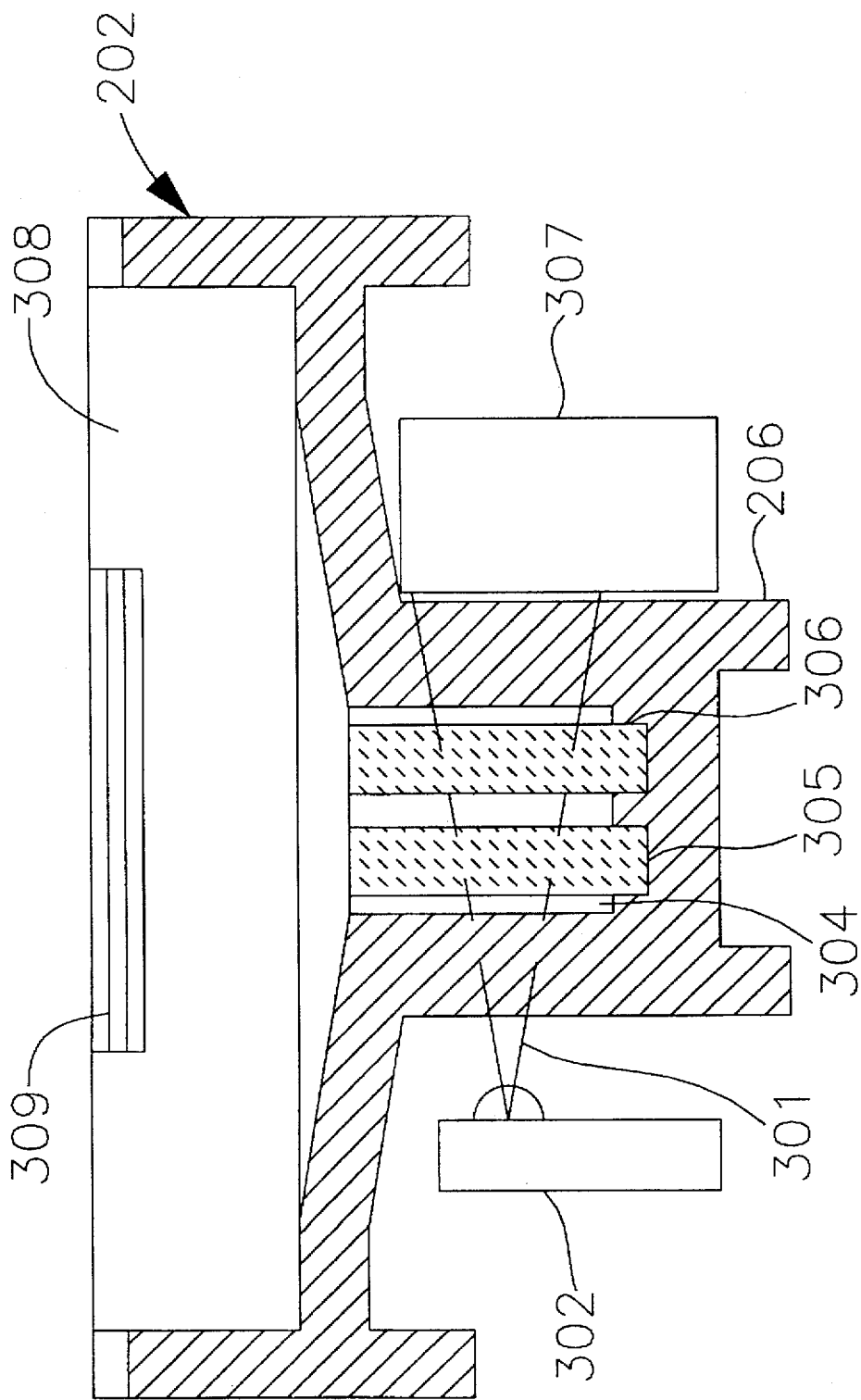
FIG. 4 is a semi-schematic cross section of a carbon monoxide sensor unit incorporating carbon monoxide sensors constructed according to principles of this invention.

The sensor unit 203 is illustrated in greater detail in FIG. 4. Light 301 is generated by a light source 302, such as a light emitting diode, a laser diode, or other compact light source positioned in the measurement unit adjacent to the sensor housing 206. The light 301 passes through a sensor holding area 304 which may contain either a single sensor 305 or multiple sensors 305 and 306. The criteria for selecting whether one or multiple sensors are used depends on variables such as temperature and humidity levels of the gas and the response to CO desired. The light passing through the sensor 305 or sensors 305 and 306 is then detected by a photodiode 307 or other light detecting device in the measurement unit.

Figure 8:
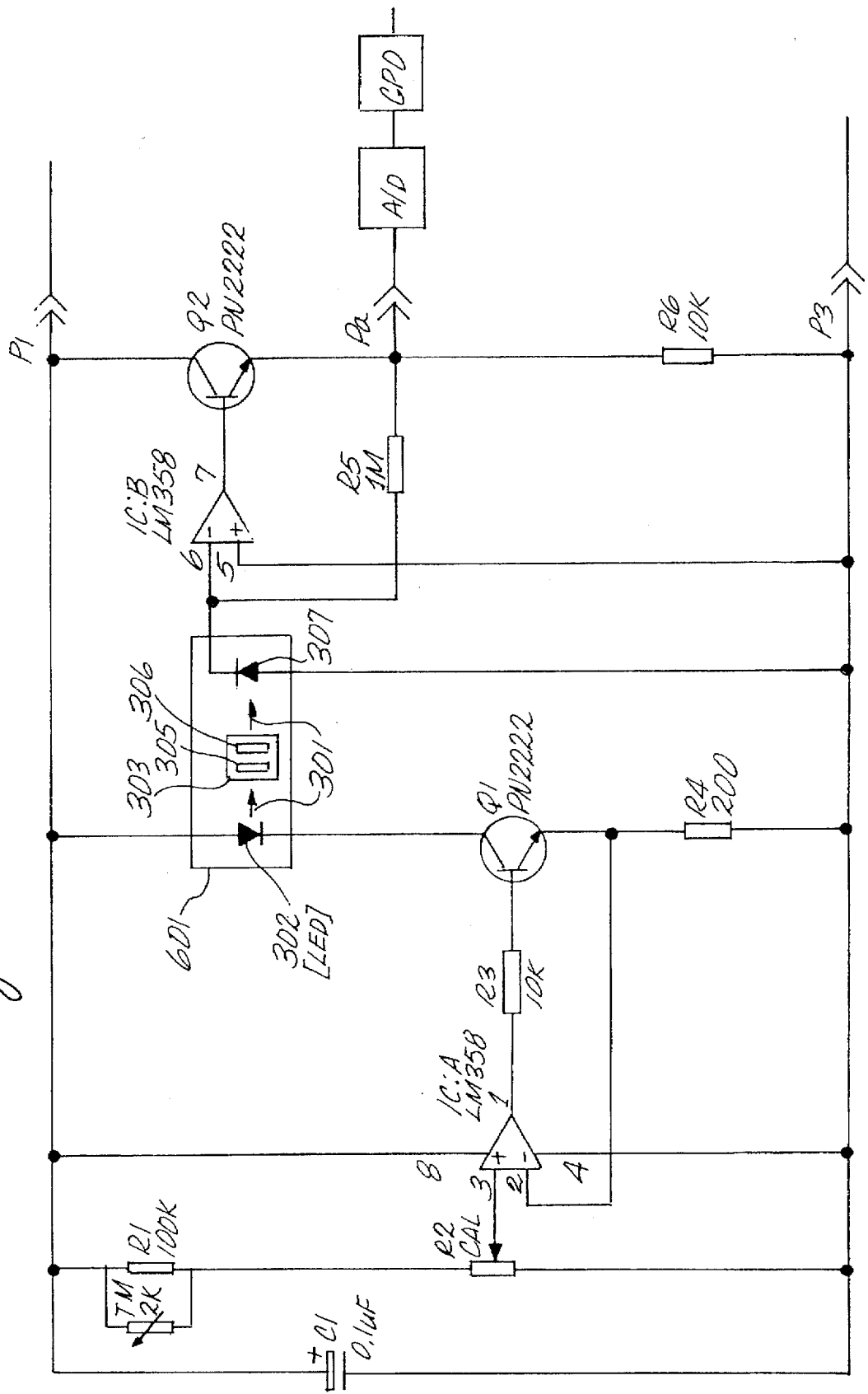
FIG. 8 is a detailed schematic circuit diagram for a sensor unit reader for implementing the present invention.

When a sensor 305 or sensors 305 and 306 are exposed to gas containing CO they darken, there by reducing the amount of light transmitted. The amount of light transmitted and thus detected by the photodiode 307 is converted into a raw data signal that is sent to a data processing unit 605 (FIG. 8).

The sensor unit 203 has a rectangular cavity 308 that fits sufficiently snugly over the adapter unit to be held in place by friction augmented by shallow ridges 309. The sensor unit can be removed when exhausted by momentary pressurization of the recirculation system or by manually pulling on the unit.

Single or multiple sensors may be used in the sensor unit depending on the expected temperature and humidity levels of the gas and the response to CO desired. The following working example is one of many possible types of sensor units that a person knowledgeable in the art, given principles of this invention, can employ. Preferably, one employs a non-regenerating sensor unit that responds to CO in moderate temperature and humidity can be made by using a single non-regenerating sensor as described in greater detail hereinafter.

A feature of the sensor unit 303 is that it is designed to fit onto the base of either an in-line or side-stream adapter units described in more detail below in FIGS. 5 and 6 and in FIG. 7, respectively. This allows for the anesthesiologist or other users of this invention to easily select the sensor unit that best suits the conditions under which CO needs to be detected.

An in-line adapter unit made according to principles of this invention is illustrated in FIGS. 5 and 6. The unit has an adapter base 401 which is designed to fit into the sensor unit cavity 308 as shown in FIG. 4, a handling lip 402 and a cylindrical portion 403 that is designed to fit into a commercially available T-piece available from anesthesia gas machine accessory manufacturers as shown in FIG. 2. When the in-line adapter is used, anesthesia gas flows through the run of the T-piece and exposes the sensor unit connected to the branch of the T-piece to anesthesia gas. The sensor is thus in continuous fluid communication with the anesthesia gas stream.

The hollow center portion of the adapter unit forms an absorbent chamber 404 that has small holes 405 in one end so that gas can pass into the sensor unit housing after passing through the absorbent chamber. The absorbent chamber can be left empty or can be filled with a variety of absorbing materials such as silica-gel, anhydrous salts, molecular sieves, or mixtures of these. In one embodiment of the invention a metal wire coil was inserted into the absorbent chamber and a small electrical current applied to heat the wire in order to dry the gas in the chamber. A retaining disk 406 with small holes is designed to fit into the end of the absorbent chamber 404 to prevent materials placed in the chamber from coming out.

An adapter for side-stream detection of CO is illustrated in FIG. 7. The unit is similar in construction to the in-line adapter, but has several unique features. The adapter base 501, handling lip 502 and the cylindrical section 503 are essentially the same as for the in-line adapter unit. The absorbent chamber 504 has a similar role as previously described but has been fitted with a gas flow separator 505 or baffle. The gas flow separator 505 directs the inflowing gases as indicated by an arrow 506 into the sensor unit and then back out of the sensor unit as indicated by an arrow 507 and into a gas exit chamber 508 that effectively makes the side-stream adapter a T.

From the gas exit chamber 508 the gas is drawn out by a vacuum pump 509 through a side-stream tubing adapter 510 and through commercially available side-stream tubing 511 that is connected to the pump 509. One advantage of the side-stream adapter is that gas is constantly flowing through the sensor unit, thus exposing the sensors to a separate stream of gas, unlike the in-line adapter which relies on diffusion. An additional advantage is that the gas passing by the sensor is not subsequently inhaled by the patient.

A detailed schematic drawing of the circuit used in the for determining carbon monoxide exposure is given in FIG. 8. The measurement unit 204 is designed to accept the sensor housing 206 thus aligning the sensor holding area, which contains either a single sensor 305 or multiple sensors 305 and 306, in the light path between the light source 302 and the photodiode 307 as previously described in relation to FIG. 4. The circuit to generates a raw data signal 602 from the photodiode signal, which is sent to a analog to digital converter 603 which changes the raw data signal into a digital signal 604.

The digital signal is sent to a data processing unit 605 comprising hardware and software to calculate, store and display useful information related to the optical characteristics of the sensor unit. The data processing unit calculates the concentration of CO based on the rate of change of sensor darkening. From the rate of change of the measured optical characteristics, the concentration of carbon monoxide and cumulative CO exposure can be calculated using the relationship in Beer's Law and an empirically derived rate constant for a particular sensor unit chemical formulation.

It is often desirable to use a non-regenerating sensor in the anesthesia apparatus so that total CO exposure over the course of an operation can be evaluated. The useful life for a sensor as employed in practice of this invention is sufficient for most operations unless an unusual amount of CO is present. In the event a sensor becomes exhausted, the sensor can be replaced during the operation for continued monitoring of CO exposure. Such sensors are employed once and discarded when partially or completely exhausted.

The non-regenerating sensor previously mentioned is made from a porous semi-transparent substrate (i.e., the substrate is sufficiently transmissive to light to permit detection of the transmitted light by a photodiode or some other light detecting device) that has been impregnated or coated with a non-regenerating chemical reagent containing a mixture of at least one of the compounds from each of the following Groups 1–3:

Group 1: Palladium compounds selected from the group consisting of palladium sulfate; palladium sulfite; palladium pyrosulfite; palladium chloride; palladium bromide; palladium iodide; palladium perchlorate; calcium tetrachloropallidate; palladium chloride dihydrate; palladium bromide dihydrate; acids of the tetrachloropallidate, tetrabromopallidate, dibromodichloropallidate, bromotrichloropallidate, tribromochloropallidate anions; sodium salts of the tetrachloropallidate, tetrabromopallidate, dibromodichloropallidate, bromotrichloropallidate, tribromochloropallidate anions; potassium salts of the tetrachloropallidate, tetrabromopallidate, dibromodichloropallidate, bromotrichloropallidate, tribromochloropallidate anions; and mixtures thereof;

Group 2: Molybdenum compounds selected from the group consisting of silicomolybdic acid; salts of silicomolybdic acid; phosphomolybdic acid; salts of phosphomolybdic acid; molybdenum trioxide; heteropolyacids of molybdenum containing vanadium, copper, tungsten, and mixtures thereof; ammonium molybdate; alkali metal and alkaline earth salts of the molybdate anion; heteropolymolybdates; and mixtures thereof;

Group 3: Acids of the chloride, bromide, sulfate, sulfite, perchlorate, and trifluoromethansulfonate anions; alkali and alkaline earth salts of the chloride; bromide, sulfate, bisulfate, sulfite, bisulfite, perchlorate, and trifluoromethanesulfonate anions; and mixtures thereof.

The mole ratio ranges for the components of the reagent solution used to form the non-regenerating sensor are Group 1: Group 2=1:0.001 to 1:0.5, and Group 1: Group 3=1:0.1 to 1:10. Preferably, the compound from Group 1 comprises palladium chloride, the compound from Group 2 comprises silicomolybdic acid, and compounds from Group 3 comprise hydrochloric acid and sulfurous acid.

The non-regenerative sensor composition avoids use of copper compounds which would cause the sensor to be self-regenerative. The sensor chemicals are not encapsulated as has been previously described for self-regenerative sensors. Furthermore, the non-regenerative sensor includes sulfite ion, for example, in the form of sulfurous acid or the alkali metal and alkaline earth metal salts of sulfurous acid. It is postulated that the sulfite ion acts as an antioxidant which keeps the sensor from slowly regenerating itself. It is desirable to avoid self regeneration so that cumulative exposure to CO can be monitored.

Sulfite ion is believed to have an equilibrium with oxygen which is similar to the molybdenum ion which provides the change in color from yellow to blue in the sensor. The sulfite ion, however, has faster reaction kinetics and it may preferentially remove oxygen from the gas being sensed. Thus, the sulfite ion inhibits self-regeneration without affecting the molybdenum reaction. It is desirable to include some means for inhibiting self-regeneration in the composition to keep the dark color of the sensor from fading in the presence of oxygen.

The substrate used to form the sensor is chosen from, but is not limited to, materials from the following list: commercial silica-gel in bead form (available from most major suppliers of silica-gel), porous silicon dioxide such as GELSIL® made by Geltech of Alachua, Fla., porous, leached borosilicate glass such as VYCOR® "THIRSTY GLASS", Corning Glass Works, Corning, N.Y. Brand No. 7930, surface modified porous silicon dioxide such as GELSIL®, surface modified leached borosilicate glass such as VYCOR® "THIRSTY GLASS", and other porous materials. A variety of physical shapes and forms for the substrate are obtained by suitable commercial processes.

The non-regenerating sensor darkens upon exposure to CO. Therefore, the presence of CO can be quantified by comparing the optical characteristics of sensors that have been exposed to CO, with the optical characteristics of an unexposed sensors. Further, the rate of change of the darkening can be determined and used to calculate the CO concentration. In the present embodiment, the optical density of the sensors are measured. However, one knowledgeable in the art would recognize that reflectance or other means of measuring optical properties could be used.

A key property of the non-regenerating sensor is that the response to CO is not interfered with by the presence of anesthetic gases or other commonly inhaled gases. Experimental data which verifies these statements is shown in Tables 2–14 and FIGS. 9–11, where the following definitions apply:

1. Non-regenerating sensor refers to a sensor that darkens upon exposure to CO and does not regenerate itself when CO is no longer present (such as is described in the present application).

2. Self-regenerating sensor refers to a sensor that darkens upon exposure to CO and does regenerate itself when CO is no longer present, as is described in the U.S. Pat. No. 5,063,164, and in pending U.S. patent application Ser. No. 08/297,141.

3. Zero air refers to commercially available compressed air that meets the standards of purity required to be sold as "zero air".

4. 100% $O_2$ refers to commercially available compressed oxygen gas that meets the standards of purity required to be sold as "100% Oxygen".

5. 50/50 $N_2O/O_2$ refers to a equal mixture of 100% nitrous oxide gas and 100% oxygen gas that meets the standards to be sold for use as an anesthetic gas.

6. 6% Ethrane in 50/50 $N_2O/O_2$ refers to a mixture of gases in which the commercially available anesthetic gas Ethrane has been mixed as a minor component into a base gas consisting of an equal mixture of 100% nitrous oxide gas and 100% oxygen gas that meets the standards to be sold for use as an anesthetic gas.

7. 5% Halothane in 50/50 N2O/O2 refers to a mixture of gases in which the commercially available anesthetic gas Halothane has been mixed as a minor component into a base gas consisting of an equal mixture of 100% nitrous oxide gas and 100% oxygen gas that meets the standards to be sold for use as an anesthetic gas.

8. 4% Isoflurane in 50/50 N2O/O2 refers to a mixture of gases in which the commercially available anesthetic gas Isoflurane has been mixed as a minor component into a base gas consisting of an equal mixture of 100% nitrous oxide gas and 100% oxygen gas that meets the standards to be sold for use as an anesthetic gas.

9. 16% Desflurane in 50/50 N2O/O2 refers to a mixture of gases in which the commercially available anesthetic gas Desflurane has been mixed as a minor component into a base gas consisting of an equal mixture of 100% nitrous oxide gas and 100% oxygen gas that meets the standards to be sold for use as an anesthetic gas.

10. 100 ppm CO refers to a mixture of 100% carbon monoxide gas has been mixed as a minor component into a base gas of zero air.

11. Relative response is a relative measure of the raw data signal generated by the measurement unit previously described. The raw data signal at time equal to zero has been normalized to a value of 1.000.

Table 1: Response of Non-regenerating Sensor to Zero Air

Figure 9:
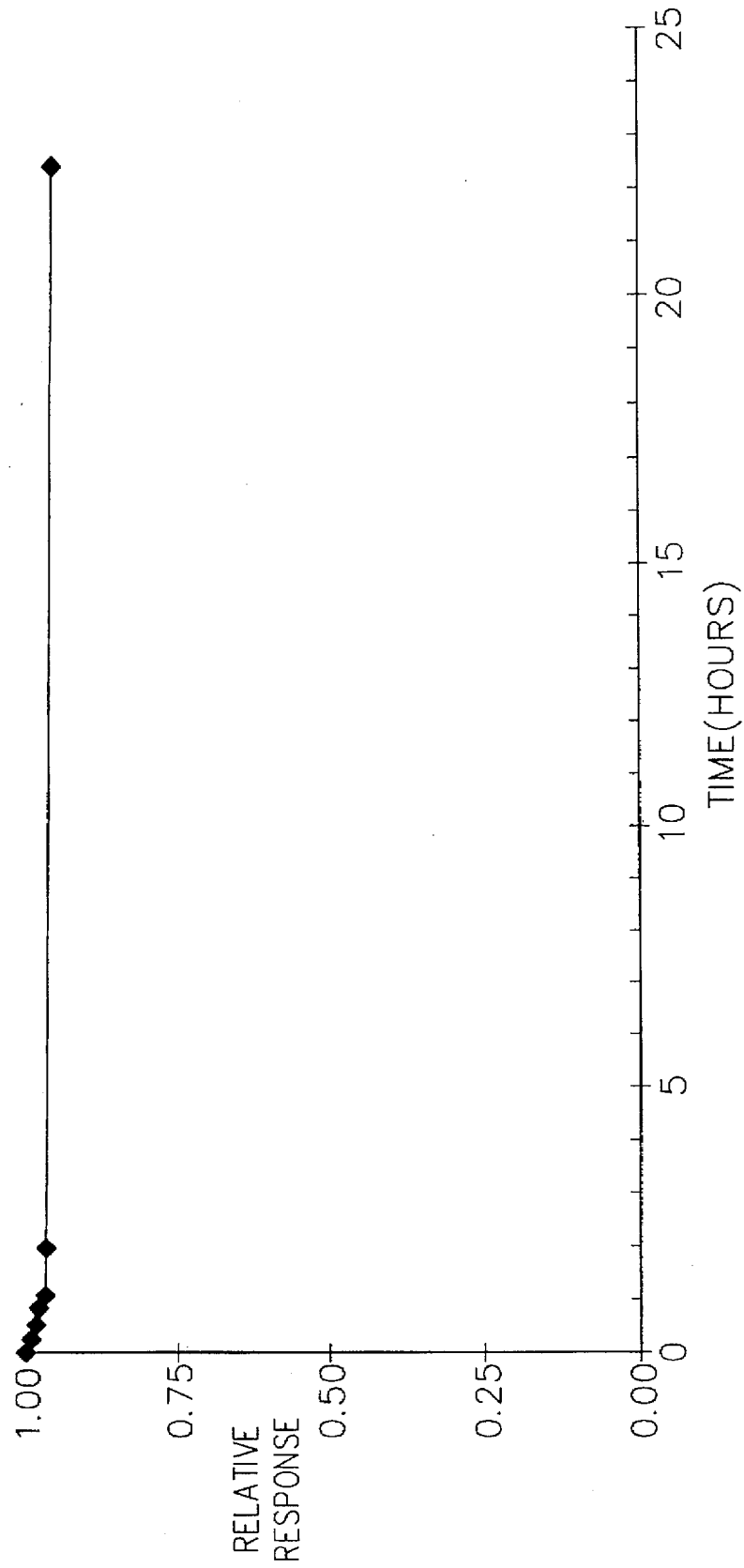
FIG. 9 is a chart illustrating in graphical form the response of the non-regenerating sensor unit subjected to zero air.

A non-regenerating sensor unit and an in-line adapter were made and combined according to principles of this invention and exposed to an atmosphere of zero air. The raw data signal at time equal to zero was normalized to a value of 1.000 and the remaining raw data signal measurements were made relative to this initial value. Very little change in the raw data signal was observed. A graphical representation of this data is given in FIG. 9, showing virtually no change in response.

| Time (Hours) | Relative Response |
|---|---|
| 0.00 | 1.000 |
| 0.25 | 0.993 |
| 0.50 | 0.990 |
| 0.75 | 0.990 |
| 1.00 | 0.985 |
| 2.00 | 0.985 |
| 22.50 | 0.982 |

Table 2: Response of Non-regenerating Sensor to 100% $O_2$

A non-regenerating sensor unit and an in-line adapter were made and combined according to principles of this invention and exposed to an atmosphere of 100% oxygen. The raw data signal at time equal to zero was normalized to a value of 1.000 and the remaining raw data signal measurements were made relative to this initial value. Very little change in the raw data signal was observed.

| Time (Hours) | Relative Response |
|---|---|
| 0.00 | 1.000 |
| 0.25 | 0.996 |
| 0.50 | 0.988 |
| 0.75 | 0.988 |
| 1.00 | 0.996 |
| 2.00 | 0.996 |
| 22.50 | 0.982 |

Table 3: Response of Non-regenerating Sensor to 50/50 $N_2O/O_2$

A non-regenerating sensor unit and an in-line adapter were made and combined according to principles of this invention and exposed to an atmosphere of 50/50 $N_2O/O_2$. The raw data signal at time equal to zero was normalized to a value of 1.000 and the remaining raw data signal measurements were made relative to this initial value. Very little change in the raw data signal was observed.

| Time (Hours) | Relative Response |
|---|---|
| 0.00 | 1.000 |
| 0.25 | 0.988 |
| 0.50 | 0.996 |
| 0.75 | 0.996 |
| 1.00 | 0.996 |
| 2.00 | 0.991 |
| 22.50 | 0.970 |

Table 4: Response of Non-regenerating Sensor to 6% Ethrane in 50/50 $N_2O/O_2$

A non-regenerating sensor unit and an in-line adapter were made and combined according to principles of this invention and exposed to an atmosphere of 6% Ethrane in 50/50 $N_2O/O_2$. The raw data signal at time equal to zero was normalized to a value of 1.000 and the remaining raw data signal measurements were made relative to this initial value. Very little change in the raw data signal was observed. A graphical representation of this data is given in FIG. 10. This graph is representative of the results obtained with other anesthesia gases mentioned in the following examples.

| Time (Hours) | Relative Response |
|---|---|
| 0.00 | 1.000 |
| 0.25 | 1.000 |
| 0.50 | 0.995 |
| 0.75 | 0.993 |
| 1.00 | 0.985 |
| 2.00 | 0.970 |
| 15.00 | 0.948 |

Table 5: Response of Non-regenerating Sensor to 5% Halothane in 50/50 $N_2O/O_2$ A non-regenerating sensor unit and an in-line adapter were made and combined according to principles of this invention and exposed to an atmosphere of 5% Halothane in 50/50 $N_2O/O_2$. The raw data signal at time equal to zero was normalized to a value of 1.000 and the remaining raw data signal measurements were made relative to this initial value. Very little change in the raw data signal was observed.

| Time (Hours) | Relative Response |
|---|---|
| 0.00 | 1.000 |
| 0.25 | 0.993 |
| 0.50 | 0.988 |
| 0.75 | 0.983 |
| 1.00 | 0.978 |
| 2.00 | 0.970 |
| 24.00 | 0.938 |

Table 6: Response of Non-regenerating Sensor to 4% Isoflurane in 50/50 $N_2O/O_3$ A non-regenerating sensor unit and an in-line adapter were made and combined according to principles of this invention and exposed to an atmosphere of 4% Isoflurane in 50/50 $N_2O/O_2$. The raw data signal at time equal to zero was normalized to a value of 1.000 and the remaining raw data signal measurements were made relative to this initial value. Very little change in the raw data signal was observed.

| Time (Hours) | Relative Response |
|---|---|
| 0.00 | 1.000 |
| 0.25 | 0.998 |
| 0.50 | 0.998 |
| 0.75 | 0.990 |
| 1.00 | 0.988 |
| 2.00 | 0.988 |
| 24.00 | 0.920 |

Table 7: Response of Non-regenerating Sensor to 16% Desflurane in 50/50 $N_2O/O_2$ A non-regenerating sensor unit and an in-line adapter were made and combined according to principles of this invention and exposed to an atmosphere of 16% Desflurane in 50/50 $N_2O/O_2$. The raw data signal at time equal to zero was normalized to a value of 1.000 and the remaining raw data signal measurements were made relative to this initial value. Very little change in the raw data signal was observed.

| Time (Hours) | Relative Response |
|---|---|
| 0.00 | 1.000 |
| 0.25 | 1.000 |
| 0.50 | 0.995 |
| 0.75 | 0.993 |
| 1.00 | 0.993 |
| 2.00 | 0.990 |
| 8.00 | 0.985 |
| 23.00 | 0.848 |

Table 8: Response of Non-regenerating Sensor to 100 ppm CO in Zero Air

A non-regenerating sensor unit and an in-line adapter were made and combined according to principles of this invention and exposed to an atmosphere of 100 ppm CO in zero air. The raw data signal at time equal to zero was normalized to a value of 1.000 and the remaining raw data signal measurements were made relative to this initial value. Very little change in the raw data signal was observed before the injection of CO. After the injection of CO, the raw data signal rapidly changes and eventually levels out as the CO is consumed by the chemical reactions occurring between the sensor and the CO gas. A graphical representation of this data is given in FIG. 11.

| Time (Min.) | Relative Response | Notes |
|---|---|---|
| 0.0 | 1.000 | |
| 0.8 | 1.010 | |
| 1.7 | 1.005 | |
| 2.5 | 1.010 | |
| 3.3 | 1.008 | |
| 4.2 | 1.008 | |
| 5.0 | 1.008 | CO injected |
| 5.8 | 0.993 | |
| 6.7 | 0.950 | |
| 7.5 | 0.915 | |
| 8.3 | 0.898 | |
| 9.2 | 0.885 | |
| 10.0 | 0.870 | |
| 15.0 | 0.800 | |
| 20.0 | 0.775 | |
| 25.0 | 0.758 | |
| 30.0 | 0.738 | |
| 35.0 | 0.728 | |
| 40.0 | 0.728 | |
| 45.0 | 0.725 | |
| 50.0 | 0.725 | |
| 60.0 | 0.715 | |
| 120 | 0.700 | |
| 1440 | 0.750 | |
| 1800 | 0.773 | |
| 1920 | 0.775 | |
| 3240 | 0.778 | |

Table 9: Response of Non-regenerating Sensor to 100 ppm CO in 100% $O_2$

A non-regenerating sensor unit and an in-line adapter were made and combined according to principles of this invention and exposed to an atmosphere of 100 ppm CO in 100% $O_2$. The raw data signal at time equal to zero was normalized to a value of 1.000 and the remaining raw data signal measurements were made relative to this initial value. Very little change in the raw data signal was observed before the injection of CO. After the injection of CO, the raw data signal rapidly changes and eventually levels out as the CO is consumed by the chemical reactions occurring between the sensor and the CO gas.

| Time (Min.) | Relative Response | Notes |
|---|---|---|
| 0.0 | 1.000 | |
| 5.0 | 1.000 | |
| 10.0 | 1.000 | |
| 15.0 | 1.000 | |
| 28.3 | 1.000 | Inject CO |
| 30.0 | 0.835 | |
| 35.0 | 0.736 | |
| 40.0 | 0.700 | |
| 45.0 | 0.673 | |
| 50.0 | 0.673 | |
| 55.0 | 0.664 | |
| 60.0 | 0.654 | |
| 120.0 | 0.643 | |
| 210.0 | 0.630 | |

Table 10: Response of Non-regenerating Sensor to 100 ppm CO in 50/50 $N_2O/O_2$

A non-regenerating sensor unit and an in-line adapter were made and combined according to principles of this invention and exposed to an atmosphere of 100 ppm CO in 50/50 $N_2O/O_2$. The raw data signal at time equal to zero was normalized to a value of 1.000 and the remaining raw data signal measurements were made relative to this initial value. Very little change in the raw data signal was observed before the injection of CO. After the injection of CO, the raw data signal rapidly changes and eventually levels out as the CO is consumed by the chemical reactions occurring between the sensor and the CO gas.

| Time (Min.) | Relative Response | Notes |
|---|---|---|
| 0.0 | 1.000 | |
| 5.0 | 1.000 | |
| 10.0 | 1.000 | |
| 13.3 | 1.000 | Inject CO |
| 15.0 | 0.926 | |
| 20.0 | 0.807 | |
| 25.0 | 0.731 | |
| 30.0 | 0.696 | |
| 35.0 | 0.684 | |
| 40.0 | 0.659 | |
| 45.0 | 0.659 | |
| 50.0 | 0.647 | |
| 55.0 | 0.644 | |
| 60.0 | 0.644 | |
| 120.0 | 0.622 | |
| 180.0 | 0.620 | |

Table 11: Response of Non-regenerating Sensor to 100 ppm CO in a mixture of 6% Ethrane and 50/50 $N_2O/O_2$ A non-regenerating sensor unit and an in-line adapter were made and combined according to principles of this invention and exposed to an atmosphere of 100 ppm CO in a mixture of 6% Ethrane and 50/50 $N_2O/O_2$. The raw data signal at time equal to zero was normalized to a value of 1.000 and the remaining raw data signal measurements were made relative to this initial value. Very little change in the raw data signal was observed before the injection of CO. After the injection of CO, the raw data signal rapidly changes and eventually levels out as the CO is consumed by the chemical reactions occurring between the sensor and the CO gas.

| Time (Min.) | Relative Response | Notes |
|---|---|---|
| 0.0 | 1.000 | |
| 5.0 | 1.000 | |
| 10.0 | 1.000 | |
| 15.0 | 1.000 | Inject CO |
| 20.0 | 0.796 | |
| 25.0 | 0.731 | |
| 30.0 | 0.689 | |
| 35.0 | 0.666 | |
| 40.0 | 0.659 | |
| 45.0 | 0.652 | |
| 50.0 | 0.633 | |
| 55.0 | 0.629 | |
| 60.0 | 0.622 | |
| 120.0 | 0.603 | |
| 180.0 | 0.600 | |

Table 12: Response of Non-regenerating Sensor to 100 ppm CO in a mixture of 5% Halothane and 50/50 $N_2O/O_2$ A non-regenerating sensor unit and an in-line adapter were made and combined according to principles of this invention and exposed to an atmosphere of 100 ppm CO in a mixture of 5% Halothane in 50/50 $N_2O/O_2$. The raw data signal at time equal to zero was normalized to a value of 1.000 and the remaining raw data signal measurements were made relative to this initial value. Very little change in the raw data signal was observed before the injection of CO. After the injection of CO, the raw data signal rapidly changes and eventually levels out as the CO is consumed by the chemical reactions occurring between the sensor and the CO gas.

| Time (Min.) | Relative Response | Notes |
|---|---|---|
| 0.0 | 1.000 | |
| 5.0 | 1.000 | |
| 10.0 | 1.000 | |
| 15.0 | 1.000 | |
| 20.0 | 1.000 | Inject CO |
| 25.0 | 0.826 | |
| 30.0 | 0.773 | |
| 35.0 | 0.749 | |
| 40.0 | 0.731 | |
| 45.0 | 0.722 | |
| 50.0 | 0.715 | |
| 55.0 | 0.703 | |
| 60.0 | 0.703 | |
| 120.0 | 0.677 | |
| 180.0 | 0.630 | |

Table 13: Response of Non-regenerating Sensor to 100 ppm CO in a mixture of 4% Isoflurane in 50/50 $N_2O/O_2$ A non-regenerating sensor unit and an in-line adapter were made and combined according to principles of this invention and exposed to an atmosphere of 100 ppm CO in a mixture of 4% Isoflurane in 50/50 $N_2O/O_2$. The raw data signal at time equal to zero was normalized to a value of 1.000 and the remaining raw data signal measurements were made relative to this initial value. Very little change in the raw data signal was observed before the injection of CO. After the injection of CO, the raw data signal rapidly changes and eventually levels out as the CO is consumed by the chemical reactions occurring between the sensor and the CO gas.

| Time (Min.) | Relative Response | Notes |
|---|---|---|
| 0.0 | 1.000 | |
| 5.0 | 1.000 | |
| 10.0 | 1.000 | |
| 15.0 | 1.000 | Inject CO |
| 20.0 | 0.828 | |
| 25.0 | 0.749 | |
| 30.0 | 0.712 | |
| 35.0 | 0.690 | |
| 40.0 | 0.665 | |
| 45.0 | 0.657 | |
| 50.0 | 0.650 | |
| 55.0 | 0.638 | |
| 60.0 | 0.633 | |
| 120.0 | 0.608 | |
| 180.0 | 0.590 | |

Table 14: Response of Non-regenerating Sensor to 100 ppm CO in a mixture of 16% Desflurane in 50/50 $N_2O/O_2$ A non-regenerating sensor unit and an in-line adapter were made and combined according to principles of this invention and exposed to an atmosphere of 100 ppm CO in a mixture of 16% Desflurane in 50/50 $N_2O/O_2$. The raw data signal at time equal to zero was normalized to a value of 1.000 and the remaining raw data signal measurements were made relative to this initial value. Very little change in the raw data signal was observed before the injection of CO. After the injection of CO, the raw data signal rapidly changes and eventually levels out as the CO is consumed by the chemical reactions occurring between the sensor and the CO gas.

In a preferred embodiment of the present invention, self-regenerating and non-regenerating sensor systems are placed one after the other in the locations designated in FIG. 1 as 120, 121, and 122, 124, and 126. The sensor unit used for the self-regenerating sensor system uses a single sensor which is made according to principles described in U.S. Pat. No. 5,063,164. An in-line adapter unit is used that has a commercially available silica gel desiccant in granular form in the absorbent chamber to absorb moisture. The sensor unit used for the non-regenerating sensor system uses a single sensor which is made according to principles of this invention.

Preparation of the Non-regenerating Sensor

Non-regenerating sensors were prepared by soaking disks of porous VYCOR® glass for two days in the reagent solution described below. The sensors formed from impregnated VYCOR® glass disks were then drained followed by drying at 40° C. for 2 to 4 hours in a vacuum oven while flushing with dry nitrogen gas.

The reagent solution was prepared according to the following recipe:

$3.76 \times 10^{-3}$ moles $PdCl_2$; $5.51 \times 10^{-4}$ moles $H_4SiMo_{12}O_{40}$; $2.51 \times 10^{-3}$ moles sulfurous acid; $6.00 \times 10^{-3}$ moles hydrochloric acid; and sufficient water to bring the total solution volume to 20.00 mL.

The data presented in Tables 2–14 demonstrates that the non-regenerating sensor units do not substantially darken when exposed to a wide variety of anesthetic gas mixtures. However, the non-regenerating sensors respond rapidly and accurately upon subsequent exposure to carbon monoxide.

The sensor system is simple to adapt to existing gas delivery systems and does not require expensive equipment. Finally, the sensor system built according to principles of this invention is inexpensive to manufacture and therefore can be incorporated into the disposable components of the gas delivery system.

The carbon monoxide detection systems prepared according to principles of this invention have been specifically described and illustrated in relation to limited working embodiments for the purposes of clarity and illustration. Many modifications and variations will be apparent to those skilled in the art. Accordingly, it is to be understood that, within the scope of the appended claims, the carbon monoxide detection systems prepared according to principles of this invention may be embodied other than specifically described herein.

What is claimed is:

1. A carbon monoxide sensor system comprising a non-regenerating sensor reagent comprising a mixture of at least one compound selected from each of the following groups:

Group 1: palladium compounds selected from the group consisting of palladium sulfate; palladium sulfite; palladium pyrosulfite; palladium chloride; palladium bromide; palladium iodide; palladium perchlorate; calcium tetrachloropallidate; palladium chloride dihydrate; palladium bromide dihydrate; acids of the tetrachloropallidate, tetrabromopallidate, dibromodichloropallidate, bromotrichloropallidate, tribromochloropallidate anions; sodium salts of the tetrachloropallidate, tetrabromopallidate, dibromodichloropallidate, bromotrichloropallidate, tribromochloropallidate anions; potassium salts of the tetrachloropallidate, tetrabromopallidate, dibromodichloropallidate, bromotrichloropallidate, tribromochloropallidate anions; and mixtures thereof;

Group 2: molybdenum compounds selected from the group consisting of silicomolybdic acid; salts of silicomolybdic acid; phosphomolybdic acid; salts of phosphomolybdic acid; molybdenum trioxide; heteropolyacids of molybdenum containing vanadium, copper, tungsten, and mixtures thereof; ammonium molybdate; alkali metal and alkaline earth salts of the molybdate anion; heteropolymolybdates; and mixtures thereof;

Group 3: acids of the chloride, bromide, sulfate, sulfite, perchlorate, and trifluoromethansulfonate anions; alkali and alkaline earth salts of the chloride, bromide, sulfate, bisulfate, sulfite, bisulfite, perchlorate, and trifluoromethanesulfonate anions; and mixtures thereof; and wherein the mixture further includes an effective amount of an antioxidant compound selected from Group 3 or an additional compound that is an antioxidant to prevent self-regeneration of the sensor.

2. A carbon monoxide sensor system as recited in claim 1 wherein the non-regenerating sensor includes compounds from the Groups 1 through Group 3 wherein the mole ratio of Group 1 to Group 2 is in the range of from 1:0.001 to 1:0.5, and the mol ratio of Group 1 to Group 3 is in the range of from 1:0.1 to 1:10.

3. A carbon monoxide sensor system as recited in claim 1 wherein the compound from Group 1 comprises palladium chloride, the compound from Group 2 comprises silicomolybdic acid, and compounds from Group 3 comprise hydrochloric acid and sulfurous acid.

4. A carbon monoxide sensor system as recited in claim 1 wherein the non-regenerating sensor comprises a semi-transparent substrate impregnated or coated with the non-regenerating sensor reagent.

5. A carbon monoxide sensor system as recited in claim 1 wherein the means for inhibiting self regeneration comprises sulfite ion.

6. A method for determining the amount of carbon monoxide in a gas stream comprising the steps of:

introducing a sensor in fluid communication with the gas stream, wherein the sensor comprises a reagent comprising a mixture of at least one compound selected from each of the following groups:

Group 1: palladium compounds selected from the group consisting of palladium sulfate; palladium sulfite; palladium pyrosulfite; palladium chloride; palladium bromide; palladium iodide; palladium perchlorate; calcium tetrachloropallidate; palladium chloride dihydrate; palladium bromide dihydrate; acids of the tetrachloropallidate, tetrabromopallidate, dibromodichloropallidate, bromotrichloropallidate, tribromochloropallidate anions; sodium salts of the tetrachloropallidate, tetrabromopallidate, dibromodichloropallidate, bromotrichloropallidate, tribromochloropallidate anions; potassium salts of the tetrachloropallidate, tetrabromopallidate, dibromodichloropallidate, bromotrichloropallidate, tribromochloropallidate anions; and mixtures thereof;

Group 2: molybdenum compounds selected from the group consisting of silicomolybdic acid; salts of silicomolybdic acid; phosphomolybdic acid; salts of phosphomolybdic acid; molybdenum trioxide; heteropolyacids of molybdenum containing vanadium, copper, tungsten, and mixtures thereof; ammonium molybdate; alkali metal and alkaline earth salts of the molybdate anion; heteropolymolybdates; and mixtures thereof;

Group 3: acids of the chloride, bromide, sulfate, sulfite, perchlorate, and trifluoromethansulfonate anions; alkali and alkaline earth salts of the chloride, bromide, sulfate, bisulfate, sulfite, bisulfite, perchlorate, and trifluoromethanesulfonate anions; and mixtures thereof; and further comprising an effective amount of an antioxidant compound selected from Group 3 or an additional compound that is an antioxidant to prevent regeneration of the sensor;

determining changes in optical characteristics of the sensor during exposure to the gas stream; and determining the amount of carbon monoxide in the gas stream as a function of changes in the optical characteristics.

7. A method as recited in claim 6 wherein the antioxidant comprises sulfite ion.

8. A non-generating sensor for detecting carbon monoxide in a gas stream comprising:

a semi-transparent substrate, a non-generating sensor reagent impregnated into the substrate for forming a non-regenerating sensor, the reagent consisting essentially of a mixture of at least one compound selected from each of the following groups:

Group 1: palladium compounds selected from the group consisting of palladium sulfate; palladium sulfite; palladium pyrosulfite; palladium chloride; palladium bromide; palladium iodide; palladium perchlorate; calcium tetrachloropallidate; palladium chloride dihydrate; palladium bromide dihydrate; acids of the tetrachloropallidate, tetrabromopallidate, dibromodichloropallidate, bromotrichloropallidate, tribromochloropallidate anions; sodium salts of the tetrachloropallidate, tetrabromopallidate, dibromodichloropallidate, bromotrichloropallidate, tribromochloropallidate anions; potassium salts of the tetrachloropallidate, tetrabromopallidate, dibromodichloropallidate, bromotrichloropallidate, tribromochloropallidate anions; and mixtures thereof;

Group 2: molybdenum compounds selected from the group consisting of silicomolybdic acid; salts of silicomolybdic acid; phosphomolybdic acid; salts of phosphomolybdic acid; molybdenum trioxide; heteropolyacids of molybdenum containing vanadium, copper, tungsten, and mixtures thereof; ammonium molybdate; alkali metal and alkaline earth salts of the molybdate anion; heteropolymolybdates; and mixtures thereof; and Group 3: acids of the chloride, bromide, sulfate, sulfite, perchlorate, and trifluoromethansulfonate anions; alkali and alkaline earth salts of the chloride, bromide, sulfate, bisulfate, sulfite, bisulfite, perchlorate, and trifluoromethanesulfonate anions; and mixtures thereof; and further comprising an effective amount of an antioxidant compound selected from Group 3 or an additional compound that is an antioxidant to prevent self-regeneration of the sensor.

9. A non-regenerating sensor for detecting carbon monoxide in a gas stream as recited in claim 8 wherein the compound from Group 1 comprises palladium chloride, the compound from Group 2 comprises silicomolybdic acid, and the compounds from Group 3 comprise hydrochloric acid and sulfurous acid.

10. A non-regenerating sensor for detecting carbon monoxide in a gas stream as recited in claim 8 wherein the semitransparent substrate is selected from the group consisting of silica gel beads, porous silicon dioxide, porous leached borosilicate glass, surface modified porous silicon dioxide, and surface modified leached borosilicate glass.

* * * * *